(12) United States Patent
Suzuki et al.

(10) Patent No.: US 10,239,879 B2
(45) Date of Patent: Mar. 26, 2019

(54) PROCESS FOR PRODUCING PURINONE DERIVATIVE

(71) Applicant: ONO PHARMACEUTICAL CO., LTD., Osaka (JP)

(72) Inventors: Ryo Suzuki, Osaka (JP); Atsushi Hiramatsu, Osaka (JP); Motoaki Tateyama, Fukui (JP); Hideyuki Sasahara, Fukui (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/564,535

(22) PCT Filed: Apr. 8, 2016

(86) PCT No.: PCT/JP2016/061595
§ 371 (c)(1),
(2) Date: Oct. 5, 2017

(87) PCT Pub. No.: WO2016/163531
PCT Pub. Date: Oct. 13, 2016

(65) Prior Publication Data
US 2018/0079751 A1    Mar. 22, 2018

(30) Foreign Application Priority Data
Apr. 9, 2015  (JP) ................. 2015-080351

(51) Int. Cl.
| C07D 473/18 | (2006.01) |
| C07D 403/12 | (2006.01) |
| C07D 239/42 | (2006.01) |
| C07D 473/34 | (2006.01) |

(52) U.S. Cl.
CPC ......... *C07D 473/18* (2013.01); *C07D 239/42* (2013.01); *C07D 403/12* (2013.01); *C07D 473/34* (2013.01); *Y02P 20/55* (2015.11)

(58) Field of Classification Search
None
See application file for complete search history.

(56) References Cited

U.S. PATENT DOCUMENTS

| 7,071,199 B1 | 7/2006 | Hirst et al. |
| 8,557,803 B2 | 10/2013 | Yamamoto et al. |
| 8,940,725 B2 | 1/2015 | Yamamoto et al. |
| 2003/0171360 A1 | 9/2003 | Gross et al. |
| 2008/0076921 A1 | 3/2008 | Honigberg et al. |
| 2013/0079327 A1 | 3/2013 | Yamamoto et al. |
| 2013/0217880 A1 | 8/2013 | Yamamoto et al. |
| 2014/0303191 A1 | 10/2014 | Buggy et al. |
| 2014/0330015 A1 | 11/2014 | Yamamoto et al. |
| 2015/0125446 A1 | 5/2015 | Klein et al. |

FOREIGN PATENT DOCUMENTS

| CA | 2800523 | 12/2011 |
| CA | 2857150 | 6/2013 |
| JP | 10-77271 | 3/1998 |
| JP | 2003-509427 | 3/2003 |
| JP | 2010-504324 | 2/2010 |
| WO | 2001/019828 | 3/2001 |
| WO | 2003/037890 | 5/2003 |
| WO | 2005/011597 | 2/2005 |
| WO | 2007/142755 | 12/2007 |
| WO | 2008/060301 | 5/2008 |
| WO | 2008/121742 | 10/2008 |
| WO | 2010/009342 | 1/2010 |
| WO | 2011/018224 | 2/2011 |
| WO | 2011/152351 | 12/2011 |
| WO | 2013/081016 | 6/2013 |
| WO | 2014/081712 | 5/2014 |
| WO | 2014/194254 | 12/2014 |
| WO | 2016/024230 | 2/2016 |

OTHER PUBLICATIONS

Wagmare, Anirudha. Review Journal of Chemistry (2014) vol. 4 No. 2 53-131.*
International Search Report dated Jan. 29, 2013 in International (PCT) Application No. PCT/JP2012/080769.
International Preliminary Report on Patentability and Written Opinion dated Jun. 3, 2014 in International (PCT) Application No. PCT/JP2012/080769.
International Search Report dated Aug. 16, 2011 in International (PCT) Application No. PCT/ JP2011/062377.
Vetrie, David, et al., "The gene involved in X-linked agammaglobulinaemia is a member of the src family of protein-tyrosine kinases", Nature, vol. 361, Jan. 21, 1993, pp. 226-233.
Uckun, Fatih M., et al., "Burton's Tyrosine Kinase as a New Therapeutic Target", Anti-Cancer Agents in Medicinal Chemistry, vol. 7, 2007, pp. 624-632.
Supplementary European Search Report dated Sep. 19, 2013 in European Application No. 11 78 9754.
Anderson, Chem. and Biol., vol. 10, 2003, pp. 787-797.
CAS RN 1222785810, entered STN May 13, 2010.
Yasuhiro et al., "ONO-4059, a novel oral Bruton's tyrosine kinase (Btk) inhibitor that demonstrates potent pharmacodynamic activity through Phosphorylated Btk (P-Btk) inhibition, in addition to effective anti-tumour activity in a TMD-8 (DLBCL) xenograft model", American Association for Cancer Research Annual Meeting 2013, Abstract No. 2452.

(Continued)

*Primary Examiner* — Deepak R Rao
*Assistant Examiner* — Laura M Daniel
(74) *Attorney, Agent, or Firm* — Wenderoth, Lind, Ponack, L.L.P.

(57) ABSTRACT

According to the present invention, differently from well-known production methods, with the use of a different starting material, Ullmann condensation which may decrease the yield with an increase of a production scale can be avoided and thus 6-amino-9-[(3R)-1-(2-butynoyl)-3-pyrrolidinyl]-7-(4-phenoxyphenyl)-7,9-dihydro-8H-purin-8-one can be provided safely and stably with high reaction yield.

7 Claims, No Drawings

(56) References Cited

OTHER PUBLICATIONS

Rule et al., "A Phase I Study of the Oral Btk Inhibitor ONO-4059 in Patients With Relapsed/Refractory B-Cell Lymphoma", 55th American Society of Hematology, session: 624, program No. 4397, 2013.
Dyer et al., "The Bruton's tyrosine kinase (BTK) inhibitor ONO-4059: Single-agent activity in patients with relapsed and refractory non-GCB-DLBCL", 2014 ASCO Annual Meeting, Abstract No. 8553.
Extended European Search Report dated Apr. 1, 2015 in corresponding European Application No. 12852725.6.
Burger et al., "Safety and activity of ibrutinib plus rituximab for patients with high-risk chronic lymphocytic leukaemia: a single-arm, phase 2 study", Lancet Oncology, vol. 15, No. 10, Aug. 2014, pp. 1090-1099.
Damle et al., "Abstract 3531: Changes in immune cell populations in relapsed/refractory CLL patients treated with a Bruton's Tyrosine Kinase (BTK) Inhibitor, Ibrutinib (PCI-32765), in combination with Bendamustine and Rituximab (BR)", Cancer Research, vol. 73, No. 8, Suppl. 1, Apr. 2013, p. 3531.
Hoellenriegel et al., "In Vivo Inhibition of BCR Activation in High-Risk CLL Patients on Therapy with Bruton's Tyrosine Kinase Inhibitor Ibrutinib: Correlative Studies from an Ongoing Phase 2 Clinical Trial", Blood, vol. 120, No. 21, 2012, p. 186.
Burger et al., "The Btk Inhibitor Ibrutinib (PCI-32765) in Combination with Rituximab Is Well Tolerated and Displays Profound Activity in High-Risk Chronic Lymphocytic Leukemia (CLL) Patients", Blood, vol. 120, No. 21, 2012, p. 187.
Herter et al., "Preclinical Activity of the Type II CD20 Antibody GA101 (Obinutuzumab) Compared with Rituximab and Ofatumumab In Vitro and in Xenograft Models", Molecular Cancer Therapeutics, vol. 12, No. 10, Oct. 2013, pages 2031-2042.
Golay et al., "Glycoengineered CD20 antibody obinutuzumab activates neutrophils and mediates phagocytosis through CD16B more efficiently than rituximab", Blood, vol. 122, No. 20, Nov. 2013, pp. 3482-3491.
Sehn et al., "Randomized Phase II Trial Comparing GA101 (Obinutuzumab) with Rituximab in Patients with Relapsed CD20 Indolent B-Cell Non-Hodgkin Lymphoma: Preliminary Analysis of the GAUSS Study", Blood, vol. 118, No. 20, 2011, p. 269.
International Search Report and Written Opinion dated Jun. 12, 2015 in International Application No. PCT/EP2014/073640.
International Search Report and Written Opinion dated Jun. 30, 2015 in International Application No. PCT/JP2015/001676.
Simon Rule et al., "A Phase I Study of the Oral Btk Inhibitor ONO-4059 in Patients with Relapsed/Refractory B-Cell Lymphoma", Blood Journal, 2013, vol. 122, Issue 21, p. 4397, Abstract #676.
Ryohei Kozaki et al., "Development of a Bruton's Tyrosine Kinase (Btk) inhibitor—ONO-WG-307, a potential treatment for B-cell malignancies", Cancer Research, 2012, vol. 72, No. 8, Supp. 1, Abstract # 857.
R. Eric Davis et al., "Chronic active B-cell-receptor signaling in diffuse large B-cell lymphoma", Nature, 2010, vol. 463, pp. 88-92.
Byrn et al., "Hydrates & Solvates", Solid-State Chemistry of Drugs, Chapter 11, 1999, pp. 233-247.
Morissette et al., "High-throughput crystallization: polymorphs, salts, co-crystals and solvates of pharmaceutical solids", Advanced Drug Delivery Reviews, vol. 56, 2004, pp. 275-300.
Rouhi et al., "The Right Stuff", Science & Technology, vol. 81, No. 8, Feb. 24, 2003, pp. 32-35.
Banker et al., "Modern Pharmaceutics", Marcel Dekker, Inc., 3rd edition, 1996, 3 pages.
NIH: National Cancer Institute, Lymphoma—Patient Version, 2015, Web <http://www.cancer.gov/types/lymphoma>.
Healthline, Non-Hodgkin's Lymphoma. 2015, Web <http://www.healthline.com/health/non-hodgkins-lymphoma#ReadThisNext0>.
Office Action dated Dec. 17, 2015 in U.S. Appl. No. 14/666,496.
Stella et al., "Prodrug strategies to overcome poor water solubility," Advanced Drug Delivery Reviews 59 (2007) 677-694.
Tannheimer, "Combination of Idelalisib and ONO/GS-4059 in Lymphoma Cell Lines Sensitive and Resistant to BTK Inhibitors", Blood Journal, vol. 126, issue 23, Dec. 2015, p. 3697.
Yang, "Idelalisib: First-in-Class PI3K Delta Inhibitor for the Treatment of Chronic Lymphocytic Leukemia, Small Lymphocytic Leukemia, and Follicular Lymphoma", Clinical Cancer Research, vol. 21, No. 7, Apr. 2015, pp. 1537-1542.
International Search Report dated Jan. 11, 2016 in International (PCT) Application No. PCT/US2016/038763.
Kozaki et al., "Kinome Reprogramming in DLBCL by the BTK-Specific Inhibitor ONO-4059 Highlights Synergistic Combinations for Clinical Application", haematologica, Jun. 2014, vol. 99, No. Suppl. 1, pp. 137-138.
Lannutti et al., "CAL-101, A Specific Inhibitor of the P110DELTA Isoform of Phosphatidylinositide 3-Kinase, for the Treatment of Non-Hodgkins Lymphomas", haematologica, Jun. 2009, vol. 94, No. Suppl. 2, pp. 272-273.
Office Action dated Aug. 11, 2017 in Korean Application No. 10-2016-7014779, with English translation.
Byrd et al., "The Btk Inhibitor Ibrutinib (PCI-32765) Alone and in Combination with Rituximab for CLL or SLL", 5 Minute Journal Club (POST-ASH) (2013), Issue 2, 15 pages.
Written Opinion dated Apr. 4, 2017 in Singapore Application No. 11201603613Y.
International Search Report dated Jul. 5, 2016 in International Application No. PCT/JP2016/061595.
Meadows et al., "PI3Kδ inhibitor, GS-1101 (CAL-101), attenuates pathway signaling, induces apoptosis, and overcomes signals from the microenvironment in cellular models of Hodgkin lymphoma", BLOOD, vol. 119, No. 8, Feb. 23, 2012, pp. 1897-1900.

\* cited by examiner

PROCESS FOR PRODUCING PURINONE DERIVATIVE

TECHNICAL FIELD

The present invention relates to a method for producing a purinone derivative which is a useful production intermediate of medicaments or a useful active pharmaceutical ingredient. Particularly, the present invention relates to a production method which can provide 6-amino-9-[(3R)-1-(2-butynoyl)-3-pyrrolidinyl]-7-(4-phenoxyphenyl)-7,9-dihydro-8H-purin-8-one with good reaction yield even in an industrial production scale.

BACKGROUND ART

Purinone derivatives typified by 6-amino-9-[(3R)-1-(2-butynoyl)-3-pyrrolidinyl]-7-(4-phenoxyphenyl)-7,9-dihydro-8H-purin-8-one (hereinafter sometimes abbreviated as the present compound) have Btk inhibitory activity and are known to be medicaments useful as prophylactic and/or therapeutic agents for B-cell lymphoma and the like (see PTL 1 or 2).

In order to provide the present compound as an active pharmaceutical ingredient, various production methods have been studied. For example, a method for producing the present compound is known, as disclosed in Examples 1 to 9 of PTL 2 (hereinafter sometimes abbreviated as the well-known production method). However, the well-known production method poses four problems as described below. Namely, it has been found that there are problems such that (1) the starting material, 4,6-dichloro-5-nitropyrimidine is potentially explosive; (2) the synthesis is expensive due to tert-butyl (3R)-3-aminopyrrolidine-1-carboxylate, which is an expensive raw material used at an initial stage of the synthesis route; (3) the molecular efficiency is low due to dibenzylamine used as a raw material for introducing an amino group; and (4) in Ullmann condensation using p-phenoxyphenylboric acid during synthesis, a reduction in the reaction yield is observed as the synthesis of the present compound increases. As the well-known production method has such problems, it caused concern that when the present compound was produced in an industrial production scale, the synthesis was expensive and the reaction yield was decreased. Therefore, there is a need for a method for producing the present compound which solves the problems accompanying the well-known production method, allows inexpensive synthesis, has high reaction yield and is suitable for an industrial production scale that can stably supply the present compound.

CITATION LIST

Patent Literature

[PTL 1] WO 2011/152351
[PTL 2] WO 2013/081016

SUMMARY OF INVENTION

Technical Problem

An object of the present invention is to provide a method for producing the present compound which can solve various problems accompanying the well-known production method and is suitable for an industrial scale production, and a novel intermediate suitable for the production method.

Solution to Problem

The inventors of the present invention carried out extensive studies in order to solve the problems, and as a result, surprisingly found a method for producing the present compound addressing the problems by making improvements such as using a different starting material and avoiding Ullmann condensation, thereby completing the present invention.

Thus, the present invention relates to:
[1] A method for producing a compound represented by the general formula (H):

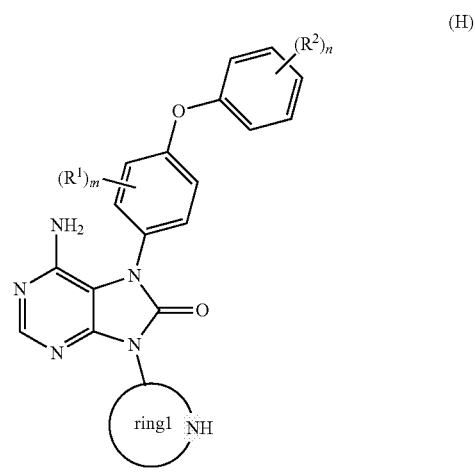

(wherein R1 represents (1) a halogen atom, (2) a C1-4 alkyl group, (3) a C1-4 alkoxy group, (4) a C1-4 haloalkyl group or (5) a C1-4 haloalkoxy group; R2 represents (1) a halogen atom, (2) a C1-4 alkyl group, (3) a C1-4 alkoxy group, (4) a nitrile, (5) a C1-4 haloalkyl group or (6) a C1-4 haloalkoxy group; ring1 represents an azetidine, pyrrolidine or piperidine ring; m represents an integer of 0 to 4; and n represents an integer of 0 to 5);
or a salt thereof,
the method including the following steps (iv) to (vii):
step (iv): subjecting a compound presented by the general formula (D):

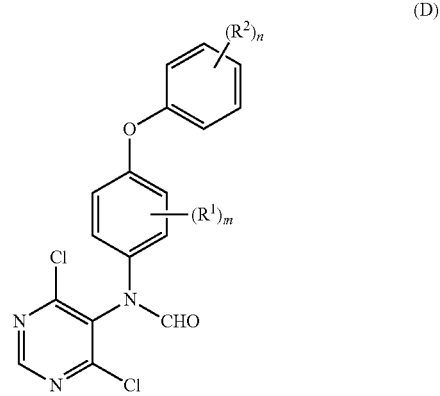

(wherein all symbols represent the same meanings as above);
or a salt thereof to a reaction with a compound represented by the general formula (a):

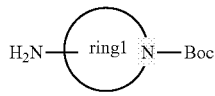

(a)

(wherein the ring1 has the same meaning as above and Boc represents a tert-butoxycarbonyl group);
or a salt thereof in the presence of a base followed by alkaline hydrolysis to produce a compound represented by the general formula (E):

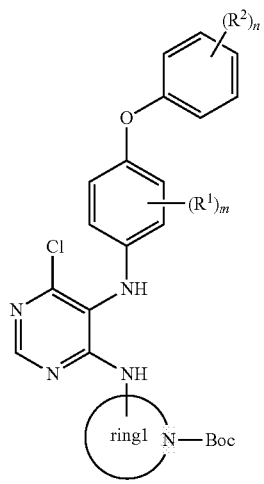

(E)

(wherein all symbols represent the same meanings as above);
or a salt thereof;
step (v): subjecting the compound represented by the general formula (E) obtained in the step (iv) or a salt thereof to a reaction with 1,1'-carbonyldiimidazole in the presence of a base to produce a compound represented by the general formula (F):

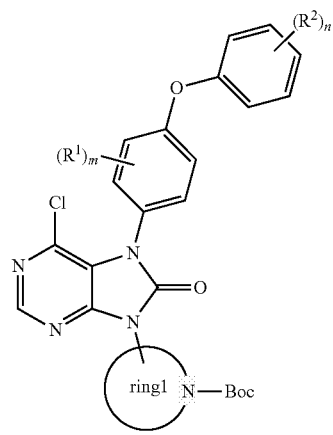

(F)

(wherein all symbols represent the same meanings as above);
or a salt thereof;
step (vi): subjecting the compound represented by the general formula (F) obtained in the step (v) or a salt thereof to a reaction with a protected amine or a salt thereof to produce a compound represented by the general formula (G):

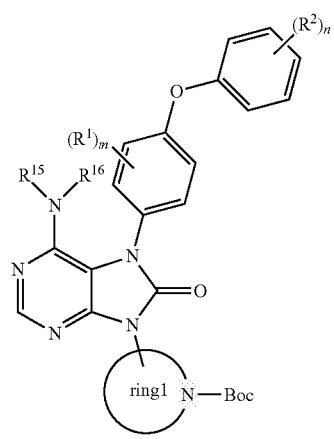

(G)

(wherein R15 and R16 respectively and independently represent a hydrogen atom, a benzyloxycarbonyl group, a t-butoxycarbonyl group, an allyloxycarbonyl group, a 1-methyl-1-(4-biphenyl)ethoxycarbonyl group, a trifluoroacetyl group, a 9-fluorenylmethoxycarbonyl group, a benzyl group, a p-methoxybenzyl group, a benzyloxymethyl group or a 2-(trimethylsilyl)ethoxymethyl group, provided that R15 and R16 do not simultaneously represent hydrogen atoms; and all other symbols represent the same meanings as above);
or a salt thereof; and
step (vii): subjecting the compound represented by the general formula (G) obtained in the step (vi) or a salt thereof to a deprotection reaction to produce the compound represented by the general formula (H) or a salt thereof;
[2] A method for producing a compound represented by the general formula (D):

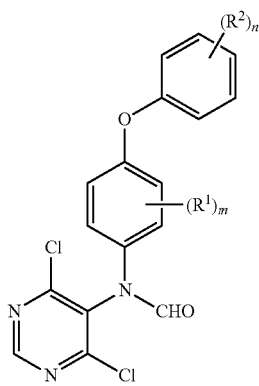

(D)

(wherein R1 represents (1) a halogen atom, (2) a C1-4 alkyl group, (3) a 01-4 alkoxy group, (4) a 01-4 haloalkyl group or (5) a C1-4 haloalkoxy group; R2 represents (1) a halogen atom; (2) a 01-4 alkyl group; (3) a C1-4 alkoxy group; (4)

a nitrile; (5) a C1-4 haloalkyl group or (6) a C1-4 haloalkoxy group; m represents an integer of 0 to 4; and n represents an integer of 0 to 5);

or a salt thereof, the method including the following steps (i) to (iii):

step (i): subjecting a compound represented by the general formula (A):

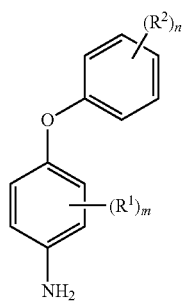

(A)

(wherein all symbols represent the same meanings as above);

or a salt thereof to a reaction with a halomalonic diester compound in the presence of a bromide salt, a phase-transfer catalyst and a base to produce a compound represented by the general formula (B):

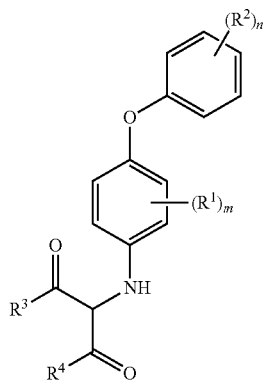

(B)

(wherein R3 and R4 respectively and independently represent a 01-3 alkoxy group; and all other symbols represent the same meanings as above);

or a salt thereof;

step (ii): subjecting the compound represented by the general formula (B) obtained in the step (i) or a salt thereof to a reaction with a formamidine salt in the presence of a base to produce a compound represented by the general formula (C):

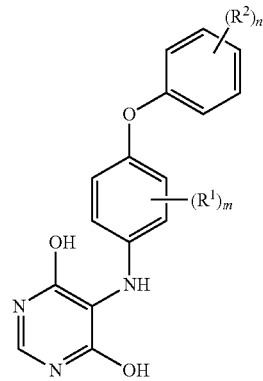

(C)

(wherein all symbols represent the same meanings as above);

or a salt thereof; and step (iii): subjecting the compound represented by the general formula (C) obtained in the step (ii) or a salt thereof to a reaction with phosphorus oxychloride in the presence of N,N-dimethylformamide to produce the compound represented by the general formula (D) or a salt thereof; [3] A method for producing a compound represented by the general formula (I):

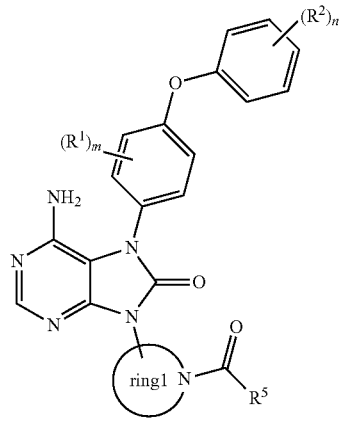

(I)

(wherein R1 represents (1) a halogen atom, (2) a C1-4 alkyl group, (3) a C1-4 alkoxy group, (4) a C1-4 haloalkyl group or (5) a C1-4 haloalkoxy group; R2 represents (1) a halogen atom, (2) a C1-4 alkyl group, (3) a C1-4 alkoxy group, (4) a nitrile, (5) a C1-4 haloalkyl group or (6) a C1-4 haloalkoxy group; R5 represents a C2-4 alkenyl group or C2-4 alkynyl group which may be substituted by 1 to 5 substituents selected from the group consisting of (1) NR6R7, (2) a halogen atom, (3) CONR8R9, (4) CO2R10 and (5) OR11; ring1 represents an azetidine, pyrrolidine or piperidine ring; m represents an integer of 0 to 4; and n represents an integer of 0 to 5);

or a salt thereof, the method including the following step (viii):

step (viii): subjecting the compound represented by the general formula (H) according to claim 1 or a salt thereof to an amidation reaction with a compound represented by the general formula (b):

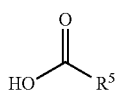

(wherein R5 represents the same meaning as above; R6 and R7 respectively and independently represent (1) a hydrogen atom or (2) a C1-4 alkyl group which may be substituted by OR12 or CONR13R14; R6 and R7 may form together with a nitrogen atom to which R6 and R7 are attached a 4- to 7-membered nitrogen-containing saturated heterocycle which may be substituted by an oxo group or a hydroxy group; R8 and R9 respectively and independently represent (1) a hydrogen atom, (2) a C1-4 alkyl group or (3) a phenyl group; R10 represents (1) a hydrogen atom or (2) a C1-4 alkyl group; R11 represents (1) a hydrogen atom, (2) a C1-4 alkyl group, (3) a phenyl group or (4) a benzotriazolyl group; R12 represents (1) a hydrogen atom or (2) a C1-4 alkyl group; and R13 and R14 respectively and independently represent (1) a hydrogen atom or (2) a C1-4 alkyl group);
or a salt thereof in the presence of 2,4,6-tripropyl-1,3,5,2,4,6-trioxatriphosphorinan-2,4,6-trioxide to produce the compound represented by the general formula (I) or a salt thereof;
[4] A method for producing the compound represented by the general formula (I) described in [3] or a salt thereof, the method including:
producing, according to the steps (i) to (iii) described in [2], the compound represented by the general formula (D) or a salt thereof from the compound represented by the general formula (A) or a salt thereof,
producing, according to the steps (iv) to (vii) described in [1], the compound represented by the general formula (H) or a salt thereof from the compound represented by the general, formula (D) or a salt thereof, and
producing, according to the step (viii) described in [3], the compound represented by the general formula (I) from the compound represented by the general formula (H) or a salt thereof;
[5] The method for producing a compound according to [3] or [4], wherein in the compound represented by the general formula (I) is 6-amino-9-[(3R)-1-(2-butynoyl)-3-pyrrolidinyl]-7-(4-phenoxyphenyl)-7,9-dihydro-8H-purin-8-one;
[6] N-(4,6-dichloropyrimidin-5-yl)-N-(4-phenoxyphenyl)formamide;
[7] tert-butyl (3R)-3-[6-(benzylamino)-8-oxo-7-(4-phenoxyphenyl)-7,8-dihydro-9H-purin-9-yl]pyrrolidine-1-carboxylate;
[8] Use of N-(4,6-dichloropyrimidin-5-yl)-N-(4-phenoxyphenyl)formamide for producing 6-amino-9-[(3R)-1-(2-butynoyl)-3-pyrrolidinyl]-7-(4-phenoxyphenyl)-7,9-dihydro-8H-purin-8-one; and
[9] Use of tert-butyl (3R)-3-[6-(benzylamino)-8-oxo-7-(4-phenoxyphenyl)-7,8-dihydro-9H-purin-9-yl]pyrrolidine-1-carboxylate for producing 6-amino-9-[(3R)-1-(2-butynoyl)-3-pyrrolidinyl]-7-(4-phenoxyphenyl)-7,9-dihydro-8H-purin-8-one.

Advantageous Effects of Invention

According to the present invention in which a different starting material is used, Ullmann condensation can be avoided and thus the present compound can be provided safely and stably with high reaction yield. Thus, the present invention is an extremely useful production method in view of the industrial productivity of the present compound which is an active pharmaceutical ingredient.

DESCRIPTION OF EMBODIMENT

The present invention is specifically described hereinafter.

In the present invention, the present compound means a compound represented by the following formula:

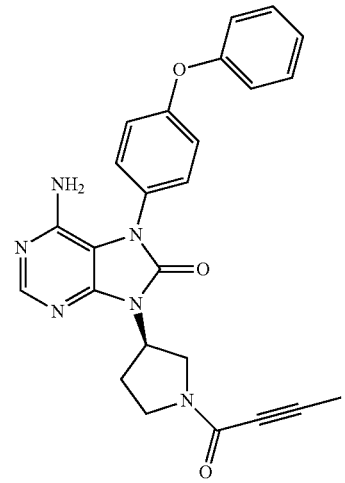

namely 6-amino-9-[(3R)-1-(2-butynoyl)-3-pyrrolidinyl]-7-(4-phenoxyphenyl)-7,9-dihydro-8H-purin-8-one.

In the present invention, the step (i) means the step in which a compound represented by the general formula (A):

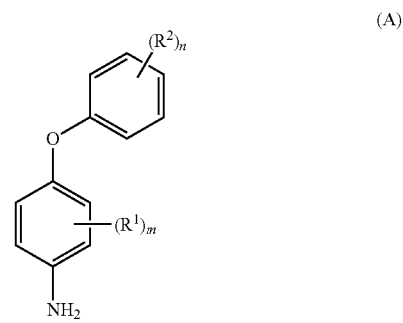

(wherein R1 represents (1) a halogen atom, (2) a C1-4 alkyl group, (3) a C1-4 alkoxy group, (4) a C1-4 haloalkyl group or (5) a C1-4 haloalkoxy group; R2 represents (1) a halogen atom, (2) a C1-4 alkyl group, (3) a 01-4 alkoxy group, (4) a nitrile, (5) a C1-4 haloalkyl group or (6) a 01-4 haloalkoxy group; m represents an integer of 0 to 4; and n represents an integer of 0 to 5);
or a salt thereof to a reaction with a halomalonic diester compound in the presence of a bromide salt, a phase-transfer catalyst and a base to produce a compound represented by the general formula (B):

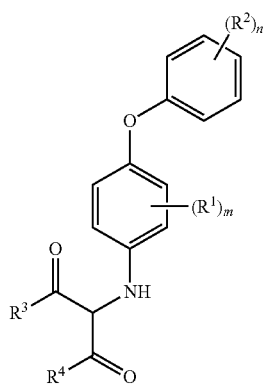

(B)

(wherein R3 and R4 respectively and independently represent a C1-3 alkoxy group; and all other symbols represent the same meanings as above);
or a salt thereof.

In the reaction in the step (i), an appropriate solvent (such as water, N,N-dimethylformamide, tetrahydrofuran, toluene, benzene, ethanol, methanol and 2-propanol) may be used as apparent to a person skilled in the art.

In the step (i), examples of the bromide salt include potassium bromide, sodium bromide and lithium bromide.

In the step (i), examples of the phase-transfer catalyst include tetrabutylammonium bromide (TBAB), tributylmethylammonium bromide, benzyltrimethylammonium bromide, phenyltributylammonium bromide, benzyltriethylammonium bromide, dodecyltrimethylammonium bromide, dodecylethyldimethylammonium bromide, myristyltrimethylammonium bromide, cetyltrimethylammonium bromide, benzyltrimethylammonium chloride, butylammonium hydrogen sulphate, among which TBAB is preferred.

Examples of the base in the step (i) include sodium hydrogen carbonate, potassium hydrogen carbonate, dipotassium hydrogen phosphate, disodium hydrogen phosphate, potassium dihydrogen phosphate, sodium dihydrogen phosphate, potassium carbonate, sodium carbonate, caesium carbonate, potassium fluoride, sodium acetate, triethylamine, N-ethyl-N,N-diisopropylamine and N,N-dimethylaniline, among which sodium hydrogen carbonate and disodium hydrogen phosphate are preferred.

In the step (i), examples of the halomalonic diester compound include dimethyl chloromalonate, diethyl chloromalonate, dimethyl bromomalonate and diethyl bromomalonate.

In the present invention, the step (ii) means a step in which the compound represented by the general formula (B) obtained in the step (i) or a salt thereof is subjected to a reaction with a formamidine salt in the presence of a base to produce a compound represented by the general formula (C):

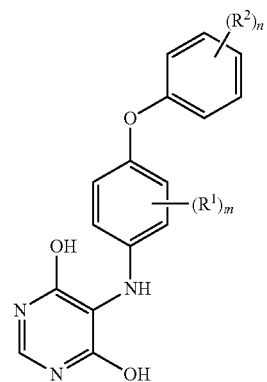

(C)

(wherein all symbols represent the same meanings as above);
or a salt thereof.

In the reaction in the step (ii), an appropriate organic solvent (such as acetonitrile, acetone, methanol, ethanol, propanol, 2-propanol, butanol, toluene, xylene, benzene, diethyl ether, tetrahydrofuran, 1,4-dioxane, N,N-dimethylformamide, N,N-dimethylacetamide and N-methyl-2-pyrrolidone) may be used as apparent to a person skilled in the art.

Examples of the base in the step (ii) include sodium methoxide and sodium ethoxide, among which sodium methoxide is preferred.

Examples of the formamidine salt in the step (ii) include formamidine acetate, formamidine hydrochloride, formamidine hydrobromide and formamidine hydroiodide, among which formamidine acetate is preferred.

In the present invention, the step (iii) means a step in which the compound represented by the general formula (C) obtained in the step (ii) or a salt thereof is subjected to a reaction with phosphorus oxychloride in the presence of N,N-dimethylformamide to produce a compound represented by the general formula (D):

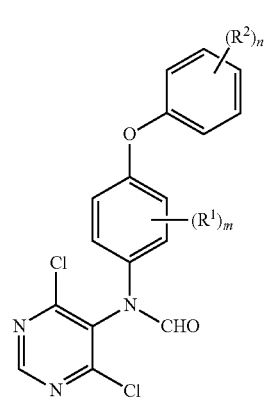

(D)

(wherein all symbols represent the same meanings as above);
or a salt thereof.

In the reaction in the step (iii), an appropriate organic solvent (such as toluene, benzene and chloroform) may be used as apparent to a person skilled in the art.

In the present invention, the step (iv) means a step in which the compound represented by the general formula (D)

obtained in the step (iii) or a salt thereof is subjected to a reaction with a compound represented by the general formula (a):

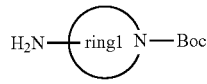

(a)

(wherein ring1 represents an azetidine, pyrrolidine or piperidine ring; and Boc represents a tert-butoxycarbonyl group);
or a salt thereof in the presence of a base followed by alkaline hydrolysis to produce a compound represented by the general formula (E):

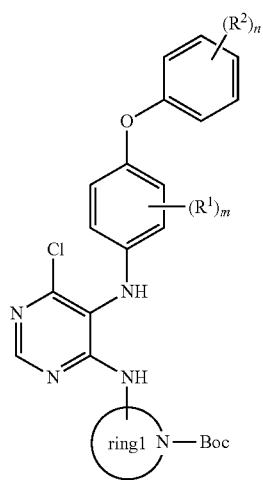

(E)

(wherein all symbols represent the same meanings as above);
or a salt thereof.

In the reaction in the step (iv), an appropriate organic solvent (such as 2-propanol, methanol, ethanol, 1-butanol, 1,4-dioxane, tetrahydrofuran and acetonitrile) may be used as apparent to a person skilled in the art.

Examples of the base in the step (iv) include triethylamine, N-ethyl-N,N-diisopropylamine, potassium carbonate and sodium hydrogen carbonate, among which triethylamine is preferred.

Examples of a solvent for alkaline hydrolysis in the step (iv) which may be used include sodium hydroxide, potassium hydroxide and lithium hydroxide.

In the present invention, the step (v) means a step in which the compound represented by the general formula (E) obtained in the step (iv) or a salt thereof is subjected to a reaction with 1,1'-carbonyldiimidazole (CDI) in the presence of a base to produce a compound represented by the general formula (F):

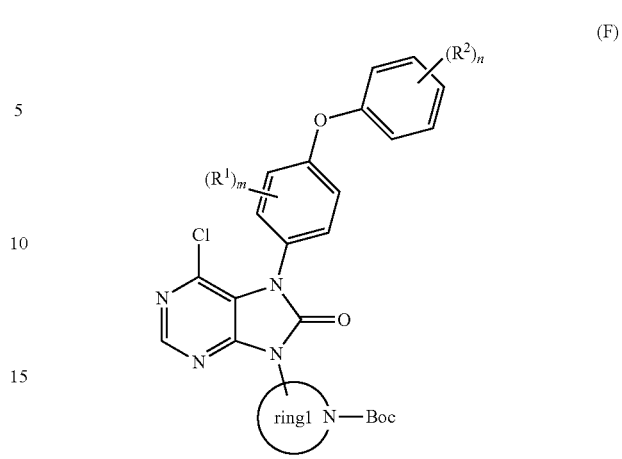

(F)

(wherein all symbols represent the same meanings as above);
or a salt thereof.

In the reaction in the step (v), an appropriate organic solvent (such as benzene, toluene, xylene, tetrahydrofuran, 1,4-dioxane, N,N-dimethylformamide, N,N-dimethylacetamide, N-methyl-2-pyrrolidone, dichloromethane, chloroform and acetonitrile) may be used as apparent to a person skilled in the art.

Examples of the base in the step (v) include 1,8-diazabicyclo[5.4.0]undec-7-ene (DBU), 1,5-diazabicyclo[4.3.0]non-5-ene (DBN), triethylamine and N-ethyl-N,N-diisopropylamine, among which DBU is preferred.

In the present invention, the step (vi) means a step in which the compound represented by the general formula (F) obtained in the step (v) or a salt thereof is subjected to a reaction with an protected amine or a salt thereof to produce a compound represented by the general formula (G):

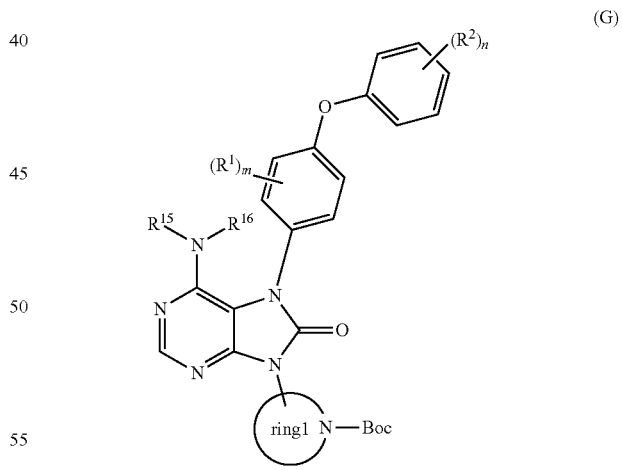

(G)

(wherein all symbols represent the same meanings as above);
or a salt thereof.

In the reaction in the step (vi), no solvent is used or an appropriate organic solvent (such as N,N-dimethylacetamide, N-methyl-2-pyrrolidone, butanol and 2-propanol) may be used as apparent to a person skilled in the art.

The protected amine in the step (vi) means NHR15R16 (R15 and R16 represent the same meanings as above). Examples thereof include benzylamine.

In the present invention, the step (vii) means a step in which the compound represented by the general formula (G) or a salt thereof is subjected to a deprotection reaction to produce a compound represented by the general formula (H):

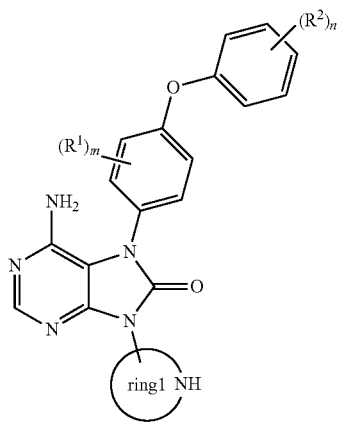

(wherein all symbols represent the same meanings as above);

or a salt thereof.

The deprotection reaction in the step (vii) means a deprotection reaction under acidic conditions and a deprotection reaction by hydrogenolysis in the presence of a palladium catalyst.

In the step (vii), the deprotection reaction under an acidic condition is carried out in an organic solvent (such as dichloromethane, chloroform, dioxane, ethyl acetate, methanol, 2-propanol, tetrahydrofuran and anisole) and in an organic acid (such as acetic acid, trifluoroacetic acid, methanesulphonic acid and p-tosylic acid) or an inorganic acid (such as hydrochloric acid and sulphuric acid) or a mixture thereof (such as hydrogen bromide/acetic acid) in the presence or absence of 2,2,2-trifluoroethanol at 0 to 100° C.

In the step (vii), the deprotection reaction by hydrogenolysis is carried out in, for example, a solvent (such as an ether solvent (such as tetrahydrofuran, dioxane, dimethoxyethane and diethyl ether), an alcohol solvent (such as methanol and ethanol), a benzene solvent (such as benzene and toluene), a ketone solvent (such as acetone, methyl ethyl ketone), an amide solvent (such as N,N-dimethylformamide), water, ethyl acetate, acetic acid or a mixed solvent of two or more of the foregoing) in the presence of a palladium catalyst (such as palladium-carbon, palladium black and palladium hydroxide-carbon) in the presence or absence of an organic acid (such as acetic acid, trifluoroacetic acid, methanesulphonic acid and p-toluenesulphonic acid) or an inorganic acid (such as hydrochloric acid, sulphuric acid, hydrobromic acid and phosphoric acid) or a mixture thereof (such as hydrogen bromide/acetic acid) in a hydrogen atmosphere under normal or increased pressure or in the presence of ammonium formate at 0 to 200° C.

In the present invention, the step (viii) means a step in which the compound represented by the general formula (H) or a salt thereof is subjected to an amidation reaction with a compound represented by the general formula (b):

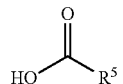

(wherein R5 represents a C2-4 alkenyl group or C2-4 alkynyl group which may be substituted by 1 to 5 substituents selected from the group consisting of (1) NR6R7, (2) a halogen atom, (3) CONR8R9, (4) CO2R10 and (5) OR11; R6 and R7 respectively and independently represent (1) a hydrogen atom or (2) a C1-4 alkyl group which may be substituted by OR12 or CONR13R14; R6 and R7 may form together with a nitrogen atom to which R6 and R7 are attached a 4- to 7-membered nitrogen-containing saturated heterocycle which may be substituted by an oxo group or a hydroxy group; R8 and R9 respectively and independently represent (1) a hydrogen atom, (2) a C1-4 alkyl group or (3) a phenyl group; R10 represents (1) a hydrogen atom or (2) a C1-4 alkyl group; R11 represents (1), a hydrogen atom, (2) a C1-4 alkyl group, (3) a phenyl group or (4) a benzotriazolyl group; R12 represents (1) a hydrogen atom or (2) a C1-4 alkyl group; and R13 and R14 respectively and independently represent (1) a hydrogen atom or (2) a C1-4 alkyl group);

or a salt thereof to produce a compound represented by the general formula (I):

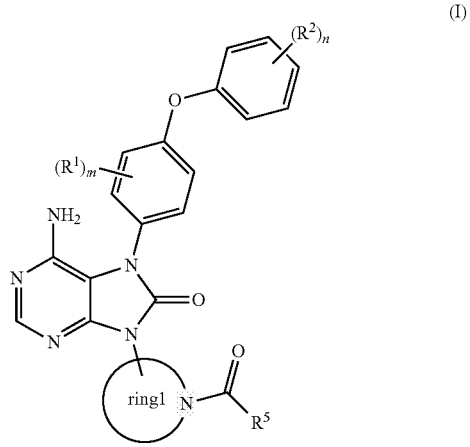

(wherein all symbols represent the same meanings as above);

or a salt thereof.

The amidation reaction in the step (viii) is suitably one in which a condensation agent is used. The method in which a condensation agent is used is preferably such that, for example, the carboxylic acid compound represented by the general formula (b) and the amine compound represented by the general formula (H) are reacted in an organic solvent (such as acetonitrile, chloroform, dichloromethane, N,N-dimethylformamide, N,N-dimethylacetamide, N-methyl-2-pyrrolidone, diethyl ether, tetrahydrofuran, pyridine, ethyl acetate and isopropyl acetate) or in the absence of a solvent, in the presence or absence of a base (such as N-methylmorpholine, pyridine, triethylamine, N-ethyl-N,N-diisopropylamine, dimethylaniline and dimethylaminopyridine) with a condensation agent (such as 2,4,6-tripropyl-1,3,5,2,4,6-trioxatriphosphorinan-2,4,6-trioxide (PPACA), 1,3-dicyclohexylcarbodiimide (DCC), 4-(4,6-dimethoxy-1,3,5-triazin- 2-yl)-4-methylmorpholinium chloride (DMT-MM), 1H-benzotriazol-1-yloxytris(dimethylamino)phosphonium hexafluorophosphate (BOP), 1H-benzotriazol-1-yloxytripyrrolidinophosphonium hexafluorophosphate (PyBOP), O-(7-aza-1H-benzotriazol-1-yl)-N,N,N',N'-tetramethyluronium hexafluorophosphate (HATU), 0-(benzotriazol-1-yl)-N,N,N',N'-tetramethyluronium hexafluorophosphate (HBTU), 1-ethyl-3-[3-(dimethylamino)propyl]carbodiimide (EDC), N,N-diisopropylcarbodiimide (DIC), 1,1'-carbonyldiimidazole (CDI), 2-chloro-1-methylpyridinium iodide and 2-chloro-4,6-dimethoxytriazine (DMT)) with or without 1-hydroxybenzotriazole (HOBt) at 0 to 40° C. Among others, N-methylmorpholine and PPACA are preferably used as the base and the condensation agent, respectively.

As used herein, the production method of the present invention encompasses any method for producing the present compound or any production intermediates thereof by performing one or more than one consecutive step of the steps (i) to (viii) described above, and particularly includes the following production methods.

(1) A method for producing the compound represented by the general formula (D) or a salt thereof including a production intermediate for the present compound, by performing the step (i)→the step (ii)→the step (iii) in this order using the compound represented by the general formula (A) or a salt thereof.

(2) A method for producing the compound represented by the general formula (H) or a salt thereof including a production intermediate for the present compound, by performing the step (vi)→the step (v)→the step (vi)→the step (vii) in this order using the compound represented by the general formula (D) or a salt thereof.

(3) A method for producing the compound represented by the general formula (I) or a salt thereof including the present compound by performing the step (viii) using the compound represented by the general formula (H) or a salt thereof.

(4) A method for producing the compound represented by the general formula (I) or a salt thereof including the present compound by performing the steps (i) to (viii) in this order using the compound represented by the general formula (A) or a salt thereof.

The present compound, the compound represented by the general formula (I) and any production intermediates thereof may be converted to salts, if necessary, according to standard methods.

In the present invention, ring1 is preferably a pyrrolidine or piperidine ring.

In the present invention, the "protected amine" is preferably benzylamine.

In the present invention, any intermediates which may be produced during the respective steps are preferred and particularly the compound represented by the general formula (D) and the compound represented by the general formula (G) are preferred. The compound represented by the general formula (D) is preferably N-(4,6-dichloropyrimidin-5-yl)-N-(4-phenoxyphenyl)formamide. The compound represented by the general formula (G) is preferably tert-butyl (3R)-3-[6-(benzylamino)-8-oxo-7-(4-phenoxyphenyl)-7,8-dihydro-9H-purin-9-yl]pyrrolidine-1-carboxylate. The general formula (I) is preferably 6-amino-9-[(3R)-1-(2-butynoyl)-3-pyrrolidinyl]-7-(4-phenoxyphenyl)-7,9-dihydro-8H-purin-8-one.

The production method of the present invention is not limited to the present compound and may be applied to, for example, examples disclosed in PTL 1. For example, Example 8, Examples 8(1) to 8(13), Examples 8(15) to 8(17) and Example 8(20) disclosed in PTL 1 are encompassed by the compound represented by the general formula (I) of the present invention, and thus the production method of the present invention may be applied to the compounds as apparent to a person skilled in the art.

In the present invention, unless otherwise stated the symbol:

indicates that the bond projects below the plane of the paper (i.e. α-configuration), the symbol:

indicates that the bond projects above the plane of the paper (i.e. β-configuration) and the symbol:

indicates that the bond is the α-configuration, the β-configuration or a mixture of the α-configuration and the β-configuration at an arbitrary ratio as apparent to a person skilled in the art.

In the present invention, a salt is preferably a pharmaceutically acceptable salt and examples thereof include alkali metal (potassium, sodium, etc.) salts, alkaline earth metal (calcium, magnesium, etc.) salts, ammonium salts, pharmaceutically acceptable organic amine (triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc.) salts, acid addition salts (inorganic acid salts (hydrochlorides, hydrobromides, hydroiodides, sulphates, phosphorates, nitrates, etc.), organic acid salts (acetates, trifluoroacetates, lactates, tartrates, oxalates, fumarates, maleates, benzoates, citrates, methanesulphonates, ethanesulphonates, benzenesulphonates, toluenesulphonates, isethionates, glucuronates, gluconates, etc.)) and the like.

EXAMPLES

The present invention is hereinafter specifically described by way of Examples which do not limit the present invention.

The solvents indicated in brackets described in chromatographic separation sections and TLC indicate elution solvents or development solvents used and the proportions are expressed in volume ratio.

The NMR data is 1H-NMR data unless otherwise stated. The solvents indicated in brackets described in NMR sections indicate solvents used for measurements.

The compounds described herein were named by using a computer programme generally according to the IUPAC nomenclature system or ACD/Name® from Advanced Chemistry Development, or named according to the IUPAC nomenclature system.

Example 1: diethyl [(4-phenoxyphenyl)amino]propanediate

To a solution of sodium bromide (204.4 kg) in water (219 L) were added tetra-n-butylammonium bromide (40 kg), sodium hydrogen carbonate (114.7 kg), diethyl chloromalonate (290.1 kg) and 4-phenoxyaniline (CAS registration number: 139-59-3) (230.0 kg) and stirred at 75° C. for 13 hours. To the reaction mixture was added ethyl acetate (230 L) followed by addition of 3.6% hydrochloric acid (460 L) while stirring. To an organic layer was added ethanol (690 L) and matured at 50° C. for 30 minutes after deposition of crystals. Water (437 L) was added and the reaction was cooled to 5° C. and matured for 2 hours. The obtained crystals were filtered, washed sequentially with a 75% ethanol aqueous solution, water and a 75% ethanol aqueous solution and dried under reduced pressure at 60° C. to obtain the titled compound (402.8 kg) having the following physical property.

TLC: Rf 0.49 (hexane:ethyl acetate=3:1).

Example 2: 5-[(4-phenoxyphenyl)amino]pyrimidine-4,6-diol

A mixture of the compound produced in Example 1 (200.5 kg), formamidine acetate (66.9 kg) and methanol (501 L) was cooled to 5° C. or below and a 28% sodium methoxide/methanol solution (405.5 kg) was added. After stirring at 40° C. for 2 hours, water (301 L) was added and pH was adjusted to around 8 with 10% hydrochloric acid. After addition of acetonitrile (201 L) and heating to 60° C., pH was adjusted to 4 to 5 with 10% hydrochloric acid followed by maturation for 1 hour. The obtained crystals were filtered, washed sequentially with a 90% methanol aqueous solution, water and a 90% methanol aqueous solution and dried under reduced pressure at 75° C. to obtain the titled compound (149.3 kg) having the following physical property.

TLC: Rf 0.35 (ethyl acetate:methanol:acetic acid=9:1:0.1).

Example 3: N-(4,6-dichloropyrimidin-5-yl)-N-(4-phenoxyphenyl)formamide

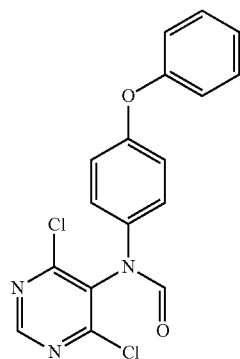 [SMILES: O=CN(c1ccc(Oc2ccccc2)cc1)c1c(Cl)ncnc1Cl]

A solution of phosphorus oxychloride (385.6 kg) in toluene (37 L) was cooled and N,N-dimethylformamide (110.3 kg) was added at 50° C. or below. The compound produced in Example 2 (148.5 kg) was then added and stirred at 90° C. for 4 hours. Water (1040 L) was placed in a separate reaction vessel and the above reaction mixture and a 35% potassium carbonate aqueous solution were simultaneously added at 40° C. while maintaining pH at around 1. Further, a 35% potassium carbonate aqueous solution was added to adjust pH to 2 to 3 and the reaction was matured for 2 hours. The obtained crystals were filtered, washed sequentially with water and 2-propanol and dried under reduced pressure at 50° C. to obtain the titled compound (163.1 kg) having the following properties.

TLC: Rf 0.40 (hexane:ethyl acetate=3:1); 1H-NMR (500 MHz, DMSO-d6): δ 9.06, 8.89, 7.45-7.33, 7.20-7.13, 7.10-7.00.

Example 4: tert-butyl (3R)-3-({6-chloro-5-[(4-phenoxyphenyl)amino]pyrimidin-4-yl}amino)pyrrolidine-1-carboxylate

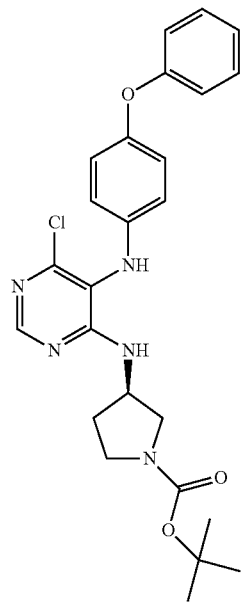 [SMILES: CC(C)(C)OC(=O)N1CC[C@@H](Nc2ncnc(Cl)c2Nc2ccc(Oc3ccccc3)cc2)C1]

A mixture of the compound produced in Example 3 (163.0 kg), 2-propanol (489 L) and triethylamine (68.7 kg) was heated to 55° C. and tert-butyl (3R)-3-aminopyrrolidine-1-carboxylate (CAS registration number: 147081-49-0) (101.2 kg) was added. After stirring for 4 hours, a 1.5 mol/L sodium hydroxide aqueous solution (702.8 kg) was added and the reaction was stirred at 50° C. for 2 hours. The reaction was cooled to room temperature, an aqueous layer was drawn, toluene (653 L) was added to an organic layer and 1 mol/L hydrochloric acid was added to adjust pH of the aqueous layer to around 2. The organic layer was washed with a mixed solution of a 20% sodium chloride solution (163 L) and a 8% sodium bicarbonate solution (82 L) and the solvent was distilled off to obtain the titled compound (218.1 kg) having the following physical property.

TLC: Rf 0.45 (hexane:ethyl acetate=1:1).

Example 5: tert-butyl (3R)-3-[6-chloro-8-oxo-7-(4-phenoxyphenyl)-7,8-dihydro-9H-purin-9-yl]pyrrolidine-1-carboxylate

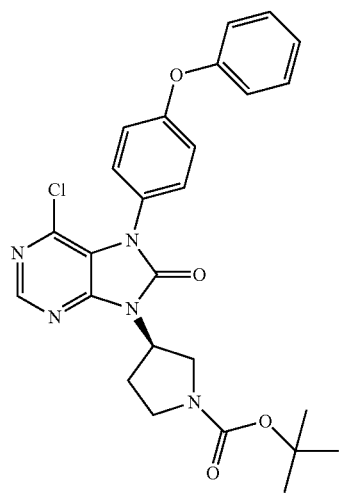 [SMILES: CC(C)(C)OC(=O)N1CC[C@@H](n2c(=O)n(-c3ccc(Oc4ccccc4)cc3)c3c(Cl)ncnc32)C1]

To a mixture of the compound produced in Example 4 (218.1 kg), toluene (436 L) and 1,1'-carbonyldiimidazole (78.5 kg) was added 1,8-diazabicyclo[5.4.0]undec-7-ene (DBU) (6.86 kg), heated to 45° C. and stirred for 2 hours. The reaction mixture was cooled to room temperature and then washed sequentially with a 5% sodium chloride solution (872 L), 2 mol/L hydrochloric acid (872 L+436 L) and a mixed solution of a 20% sodium chloride solution (327 L) and a 8% sodium bicarbonate solution (109 L) and the solvent was distilled off to obtain the titled compound (229.9 kg) having the following physical property.

TLC: Rf 0.56 (hexane:ethyl acetate=1:1).

Example 6: tert-butyl (3R)-3-[6-(benzylamino)-8-oxo-7-(4-phenoxyphenyl)-7,8-dihydro-9H-purin-9-yl]pyrrolidine-1-carboxylate

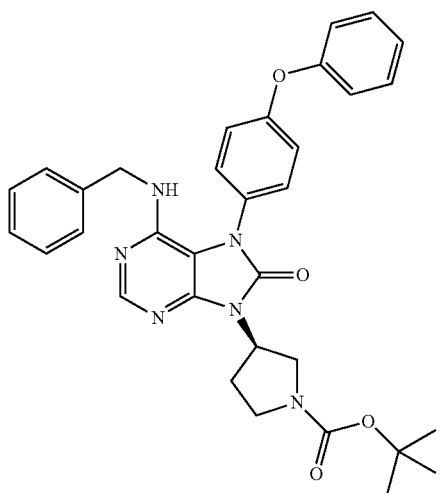 [SMILES: CC(C)(C)OC(=O)N1CC[C@@H](n2c(=O)n(-c3ccc(Oc4ccccc4)cc3)c3c(NCc4ccccc4)ncnc32)C1]

A mixture of the compound produced in Example 5 (229.9 kg) and benzylamine (242.1 kg) was heated to 115° C. and stirred for 7 hours. The reaction mixture was cooled to room temperature, water (345 L) was added thereto followed by extraction with toluene (690 L). pH of an aqueous layer was adjusted to around 2 by adding 1 mol/L hydrochloric acid to the organic layer and the aqueous layer was separated. The organic layer was washed with a 8.5% sodium chloride solution (298 L) and the solvent was distilled off to obtain the titled compound (261.9 kg) having the following physical properties.

TLC: Rf 0.35 (hexane:ethyl acetate=1:1);
1H-NMR (CDCl3): δ 8.36-8.28, 7.45-7.25, 7.24-7.13, 7.10-6.95, 5.23-5.06, 4.64, 4.30-4.21, 4.06-3.90, 3.88-3.68, 3.55-3.35, 3.05-2.80, 2.33-2.15, 1.53-1.43.

Example 7: 6-amino-7-(4-phenoxyphenyl)-9-[(3R)-pyrrolidin-3-yl]-7,9-dihydro-8H-purin-8-one dihydrochloride

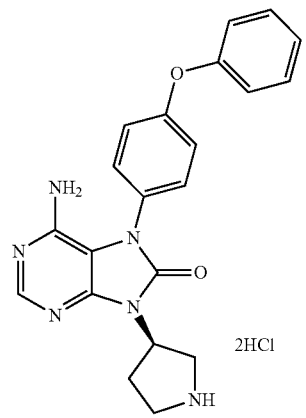 [SMILES: Nc1ncnc2c1n(-c1ccc(Oc3ccccc3)cc1)c(=O)n2[C@@H]1CCNC1]

To a mixture of the compound produced in Example 6 (261.9 kg) and methanol (1310 L) was added 36% hydrochloric acid (229.2 kg), heated to 65° C. and stirred for 2 hours. The reaction solution was cooled to room temperature and divided into 5 aliquots to each of which was added 20% palladium hydroxide-carbon (water content: 50%, 4.2 kg) and stirred under hydrogen pressure of 0.3 MPa at 60° C. for about 7 hours. The reaction solution was filtered and the combined filtrate was concentrated. Methanol was added to the concentrated residue to adjust the solution volume to 786 L. At 65° C., 2-propanol (786 L) was added followed by maturation at 65° C. for 30 minutes and 5° C. for 2 hours. The obtained crystals were filtered, washed with a mixed solution (1/1) of methanol and 2-propanol and dried under reduced pressure at 50° C. to obtain the titled compound (190.4 kg) having the following physical property.

TLC: Rf 0.30 (dichloromethane:methanol:28% aqueous ammonia=9:1:0.1).

Example 8: 6-amino-9-[(3R)-1-(2-butynoyl)-3-pyrrolidinyl]-7-(4-phenoxyphenyl)-7,9-dihydro-8H-purin-8-one

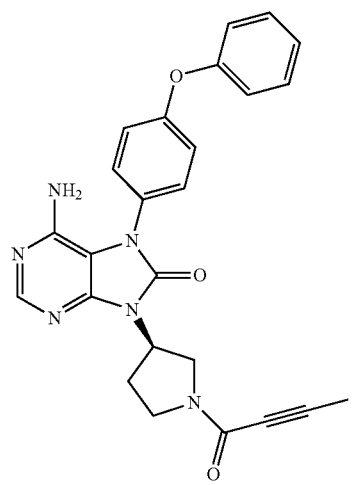 [SMILES: CC#CC(=O)N1CC[C@@H](n2c(=O)n(-c3ccc(Oc4ccccc4)cc3)c3c(N)ncnc32)C1]

A mixture of the compound produced in Example 7 (185.0 kg), 2-butynoic acid (CAS registration number: 590-93-2) (40.5 kg) and acetonitrile (463 L) was heated to 40° C. and N-methylmorpholine (243.4 kg) was added. A solution of 2,4,6-tripropyl-1,3,5,2,4,6-trioxatriphosphorinan-2,4,6-trioxide (PPACA) in 50% ethyl acetate solution (306.2 kg) was then added and the mixture was stirred for 3 hours. To the reaction mixture was added water (740 L) and extracted twice with ethyl acetate (740 L). The combined organic layer was washed sequentially with water (740 L) and a 15% sodium chloride solution (740 L) and dried after addition of anhydrous magnesium sulphate and silica gel, and the solvent was distilled off. To the residue were added acetone (235 L) and water (26 L) and heated to 50° C. After addition of methanol (185 L) and then addition of seed crystals, methanol (370 L) was further added and the reaction was matured at 50° C. for 30 minutes. Water (1110 L) was then added and the reaction was matured at 50° C. for 1 hour and 5° C. for 3 hours. The obtained crystals were filtered, washed with methanol and dried under reduced pressure at 65° C. to obtain the titled compound (160.9 kg) having the following physical properties as white crystals.

TLC: Rf 0.68 (ethyl acetate:methanol=9:1);

1H-NMR (CDCl3): δ 1.94-2.03, 2.23-2.39, 2.80-3.01, 3.50-3.63, 3.67-3.80, 3.86-4.02, 4.03-4.18, 4.23-4.33, 4.42-4.51, 5.11-5.25, 7.04-7.23, 7.34-7.45, 8.20-8.23.

Example 9: 6-amino-9-[(3R)-1-(2-butynoyl)-3-pyrrolidinyl]-7-(4-phenoxyphenyl)-7,9-dihydro-8H-purin-8-one hydrochloride

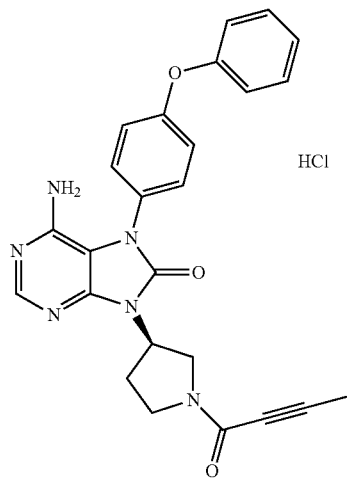 [SMILES: CC#CC(=O)N1CC[C@@H](n2c(=O)n(-c3ccc(Oc4ccccc4)cc3)c3c(N)ncnc32)C1 ; Cl]

A mixture of the compound produced in Example 8 (160.5 kg) and acetone (1364 L) was heated to 50° C. to completely dissolve the compound produced in Example 8. After addition of water (16 L) and acetone (32 L), a 4 mol/L hydrogen chloride/ethyl acetate solution (27 L) was added. After addition of seed crystals and maturation for 1.5 hours, a 4 mol/L hydrogen chloride/ethyl acetate solution (88 L) was further added and the reaction was thoroughly washed with acetone (32 L). After maturation for 30 minutes, the reaction was cooled to an inner temperature of 25° C. The obtained crystals were filtered, washed with a mixed solution (2/1) of ethyl acetate and acetone and dried under reduced pressure at 50° C. to obtain the titled compound (169.7 kg) having the following physical properties as white crystals.

TLC: Rf 0.55 (tetrahydrofuran:ethyl acetate:28% aqueous ammonia=20:12:1);

1H-NMR (CD3OD): δ 1.97-2.07, 2.38-2.52, 2.63-2.80, 3.51-3.63, 3.77-3.94, 4.00-4.19, 4.27-4.35, 5.26-5.38, 7.08-7.23, 7.38-7.52, 8.44-8.47.

Alternatively, the present compound may be produced according to the following Examples.

Example 1(1): diethyl [(4-phenoxyphenyl)amino]propanediate

To a solution of sodium bromide (106.7 kg) in water (102 L) were added tetra-n-butylammonium bromide (20.9 kg), sodium hydrogen carbonate (59.9 kg), diethyl chloromalonate (151.3 kg) and 4-phenoxyaniline (CAS registration number: 139-59-3) (120.0 kg) and stirred at 75° C. for 5 hours. To the reaction mixture was added ethyl acetate (120 L) followed by addition of 3.6% hydrochloric acid (240 L) while stirring. To an organic layer was added ethanol (360 L) and matured at 50° C. for 30 minutes after deposition of crystals. Water (228 L) was added and the reaction was cooled to 5° C. and matured for 2 hours. The obtained crystals were filtered, washed sequentially with a 75% ethanol aqueous solution, water and a 75% ethanol aqueous solution and dried under reduced pressure at 60° C. to obtain the titled compound (212 kg) having the following physical property.

TLC: Rf 0.49 (hexane:ethyl acetate=3:1).

Example 2(1): 5-[(4-phenoxyphenyl)amino]pyrimidine-4,6-diol

To a solution of the compound produced in Example 1(1) (208.0 kg) in acetonitrile (208 L) and methanol (208 L) was added a mixture of a 28% sodium methoxide/methanol solution (420.7 kg) and methanol (20.8 L). A mixture of formamidine acetate (69.4 kg) and methanol (478 L) was then added and the reaction was stirred at 40° C. for 1 hour, water (312 L) was added and pH was adjusted to around 8 with 10% hydrochloric acid. The reaction was heated to 60° C., pH was adjusted to 4 to 5 by addition of 10% hydrochloric acid followed by maturation for 1 hour. The obtained crystals were filtered, washed sequentially with a 90% methanol aqueous solution, water and a 90% methanol aqueous solution and dried under reduced pressure at 75° C. to obtain the titled compound (164.3 kg) having the following physical property.

TLC: Rf 0.35 (ethyl acetate:methanol:acetic acid=9:1:0.1).

Example 3(1): N-(4,6-dichloropyrimidin-5-yl)-N-(4-phenoxyphenyl)formamide

A solution of phosphorus oxychloride (402.4 kg) in toluene (37 L) was cooled and N,N-dimethylformamide (121.3 kg) was added at 50° C. or below. The compound produced in Example 2(1) (155.0 kg) was then added and stirred at 90° C. for 3 hours. Water (1085 L) was placed in a separate reaction vessel and the above reaction mixture and a 35% potassium carbonate aqueous solution were simultaneously added at 40° C. while maintaining pH at around 1. Further, a 35% potassium carbonate aqueous solution was added to adjust pH to 2 to 3 and the reaction was matured for 2 hours. The obtained crystals were filtered, washed sequentially with water and 2-propanol and dried under reduced pressure at 50° C. to obtain the titled compound (173.0 kg) having the following physical properties.

TLC: Rf 0.40 (hexane:ethyl acetate=3:1);
1H-NMR (500 MHz, DMSO-d6): δ 9.06, 8.89, 7.45-7.33, 7.20-7.13, 7.10-7.00.

Example 4(1): tert-butyl (3R)-3-({6-chloro-5-[(4-phenoxyphenyl)amino]pyrimidin-4-yl}amino)pyrrolidine-1-carboxylate A mixture of the compound produced in Example 3(1) (171.0 kg), 2-propanol (513 L) and triethylamine (72.1 kg) was heated to 55° C. and tert-butyl (3R)-3-aminopyrrolidine-1-carboxylate (CAS registration number: 147081-49-0) (106.1 kg) was added. After stirring for 4 hours, a 1.5 mol/L sodium hydroxide aqueous solution (737.8 kg) was added and the reaction was stirred at 50° C. for 2 hours. The reaction was cooled to room temperature, an aqueous layer was drawn, toluene (684 L) was added to an organic layer and 1 mol/L hydrochloric acid (834.5 kg) was added. The organic layer was washed with a mixed solution of a 20% sodium chloride solution (196.4 kg) and a 8% sodium bicarbonate solution (90.4 kg) and the solvent was distilled off to obtain the titled compound (228.8 kg) having the following physical property.
TLC: Rf 0.45 (hexane:ethyl acetate=1:1).

Example 5(1): tert-butyl (3R)-3-[6-chloro-8-oxo-7-(4-phenoxyphenyl)-7,8-dihydro-9H-purin-9-yl]pyrrolidine-1-carboxylate To a mixture of the compound produced in Example 4(1) (228.8 kg), toluene (458 L) and 1,1'-carbonyldiimidazole (82.4 kg) was added 1,8-diazabicyclo[5.4.0]undec-7-ene (DBU) (7.23 kg), heated to 45° C. and stirred for 2 hours. The reaction mixture was cooled to room temperature and then washed sequentially with a 5% sodium chloride solution (948 kg), 2 mol/L hydrochloric acid (948 kg+473 kg) and a mixed solution of a 20% sodium chloride solution (395 kg) and a 8% sodium bicarbonate solution (121 kg) and the solvent was distilled off to obtain the titled compound (241.2 kg) having the following physical property.
TLC: Rf 0.56 (hexane:ethyl acetate=1:1).

Example 6(1): tert-butyl (3R)-3-[6-(benzylamino)-8-oxo-7-(4-phenoxyphenyl)-7,8-dihydro-9H-purin-9-yl]pyrrolidine-1-carboxylate A mixture of the compound produced in Example 5(1) (241.2 kg) and benzylamine (254.3 kg) was heated to 115° C. and stirred for 7 hours. The reaction mixture was cooled to room temperature, 2 mol/L hydrochloric acid (849 kg) was added thereto followed by extraction with toluene (723 L). The organic layer was distilled off to obtain the titled compound (274.7 kg) having the following physical properties.
TLC: Rf 0.35 (hexane:ethyl acetate=1:1);
1H-NMR (CDCl3): δ 8.36-8.28, 7.45-7.25, 7.24-7.13, 7.10-6.95, 5.23-5.06, 4.64, 4.30-4.21, 4.06-3.90, 3.88-3.68, 3.55-3.35, 3.05-2.80, 2.33-2.15, 1.53-1.43.

Example 7(1): 6-amino-7-(4-phenoxyphenyl)-9-[(3R)-pyrrolidin-3-yl]-7,9-dihydro-8H-purin-8-one dihydrochloride To a mixture of the compound produced in Example 6(1) (274.7 kg) and methanol (1648 L) was added 36% hydrochloric acid (247.3 kg), heated to 65° C. and stirred for 2 hours. The reaction solution was cooled to room temperature and divided into 5 aliquots to each of which was added 20% palladium hydroxide-carbon (water content: 50%, 22.0 kg) and stirred under hydrogen pressure of 0.3 MPa at 60° C. for about 7 hours. The reaction solution was filtered and the combined filtrate was concentrated. Methanol was added to the concentrated residue to adjust the solution volume to 824 L. At 65° C., 2-propanol (824 L) was added followed by maturation at 65° C. for 30 minutes and 5° C. for 2 hours. The obtained crystals were filtered, washed with a mixed solution (1/1) of methanol and 2-propanol and dried under reduced pressure at 50° C. to obtain the titled compound (185.4 kg) having the following physical property.
TLC: Rf 0.30 (dichloromethane:methanol:28% aqueous ammonia=9:1:0.1).

Example 8(1): 6-amino-9-[(3R)-1-(2-butynoyl)-3-pyrrolidinyl]-7-(4-phenoxyphenyl)-7,9-dihydro-8H-purin-8-one A mixture of the compound produced in Example 7(1) (185.0 kg), 2-butynoic acid (CAS registration number: 590-93-2) (40.5 kg) and acetonitrile (463 L) was cooled to 10° C., a mixture of N-methylmorpholine (243.4 kg) and a solution of 2,4,6-tripropyl-1,3,5,2,4,6-trioxatriphosphorinan-2,4,6-trioxide (PPACA) in 50% ethyl acetate solution (306.2 kg) was added, heated to 40° C. and stirred for 3 hours. To the reaction mixture was added water (740 L) and extracted twice with ethyl acetate (370 L). The combined organic layer was washed sequentially with water (740 L) and a 15% sodium chloride solution (740 L), 85% phosphoric acid (4.62 kg) was added and the solvent was distilled off. To the residue were added acetone (222 L) and water (26 L) and heated to 50° C. After addition of water (463 L) and methanol (555 L) and then addition of seed crystals, the reaction was matured at 50° C. for 60 minutes. Water (648 L) was then added and the reaction was matured at 50° C. for 1 hour and 5° C. for 1 hour. The obtained crystals were filtered, washed with methanol and dried under reduced pressure at 65° C. to obtain the titled compound (167.7 kg) having the following physical properties as white crystals.
TLC: Rf 0.68 (ethyl acetate:methanol=9:1);
1H-NMR (CDCl3): δ 1.94-2.03, 2.23-2.39, 2.80-3.01, 3.50-3.63, 3.67-3.80, 3.86-4.02, 4.03-4.18, 4.23-4.33, 4.42-4.51, 5.11-5.25, 7.04-7.23, 7.34-7.45, 8.20-8.23.

Example 9(1): 6-amino-9-[(3R)-1-(2-butynoyl)-3-pyrrolidinyl]-7-(4-phenoxyphenyl)-7,9-dihydro-8H-purin-8-one hydrochloride A mixture of the compound produced in Example 8(1) (160.0 kg) and acetone (1280 L) was heated to 50° C. to completely dissolve the compound produced in Example 8(1). After addition of water (32 L) and acetone (112 L), a 4 mol/L hydrogen chloride/ethyl acetate solution (26 L) was added. After addition of seed crystals and maturation for 5 hours, a 4 mol/L hydrogen chloride/ethyl acetate solution (88 L) was further added and the reaction was thoroughly washed with ethyl acetate (160 L). After maturation for 30 minutes, the reaction was cooled to an inner temperature of 25° C. The obtained crystals were filtered, washed three times with a mixed solution (2/1) of ethyl acetate and acetone and dried under reduced pressure at 50° C. to obtain the titled compound (165.9 kg) having the following physical properties as white crystals.
TLC: Rf 0.55 (tetrahydrofuran:ethyl acetate:28% aqueous ammonia=20:12:1);

1H-NMR (CD3OD): δ 1.97-2.07, 2.38-2.52, 2.63-2.80, 3.51-3.63, 3.77-3.94, 4.00-4.19, 4.27-4.35, 5.26-5.38, 7.08-7.23, 7.38-7.52, 8.44-8.47.

According to the above Example 1→Example 2→Example 3→Example 4→Example 5→Example 6→Example 7→Example 8→Example 9, the yield of the present compound was 60% for example when the starting material (4-phenoxyaniline) was 230 kg. Similarly, according to Example 1(1)→Example 2(1)→Example 3(1)→Example 4(1)→Example 5(1)→Example 6(1)→Example 7(1)→Example 8(1)→Example 9(1), the yield of the present compound was 61% for example when the starting material (4-phenoxyaniline) was 120 kg. In contrast, according to the well-known production method, the yield of the present compound was 20% for example when the starting material (4,6-dichloro-5-nitropyrimidine) was 19 g and 19% when the starting material was 880 g. Therefore, according to the production method of the present invention, the yield of the present compound is high compared to the well-known production method even in an industrial production scale and the present compound can be stably provided.

INDUSTRIAL APPLICABILITY

According to the present invention, the reaction yield is high and the present compound can be stably provided. Therefore, the present invention can be a useful production method of present compound that can be used in an industrial production scale.

The invention claimed is:
1. A method for producing a compound represented by the formula (H):

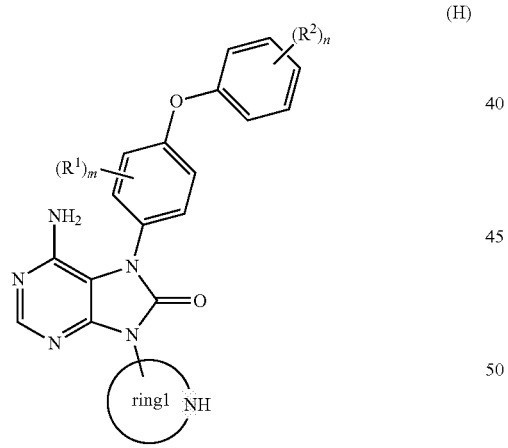

wherein R1 represents (1) a halogen atom, (2) a C1-4 alkyl group, (3) a C1-4 alkoxy group, (4) a C1-4 haloalkyl group or (5) a C1-4 haloalkoxy group; R2 represents (1) a halogen atom, (2) a C1-4 alkyl group, (3) a C1-4 alkoxy group, (4) a nitrile, (5) a C1-4 haloalkyl group or (6) a C1-4 haloalkoxy group; ring1 represents an azetidine, pyrrolidine or piperidine ring; m represents an integer of 0 to 4; and n represents an integer of 0 to 5;
or a salt thereof,
the method comprising the following steps (iv) to (vii):
step (iv): subjecting a compound represented by the formula (D):

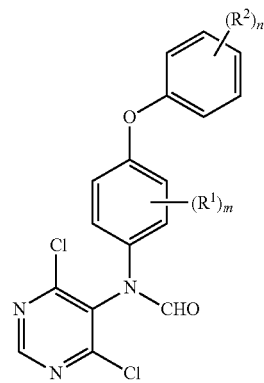

wherein all symbols represent the same meanings as above;
or a salt thereof to a reaction with a compound represented by the formula (a):

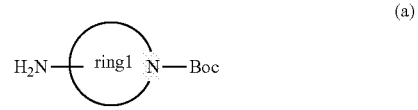

wherein ring1 has the same meaning as above and Boc represents a tert-butoxycarbonyl group;
or a salt thereof in the presence of a base followed by alkaline hydrolysis to produce a compound represented by the formula (E):

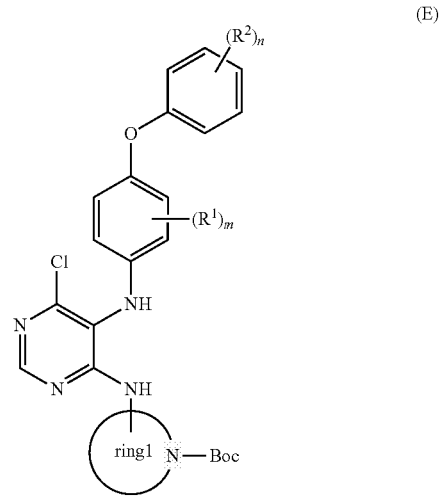

wherein all symbols represent the same meanings as above;
or a salt thereof;
step (v): subjecting the compound represented by the formula (E) obtained in the step (iv) or a salt thereof to a reaction with 1,1'-carbonyldiimidazole in the presence of a base to produce a compound represented by the formula (F):

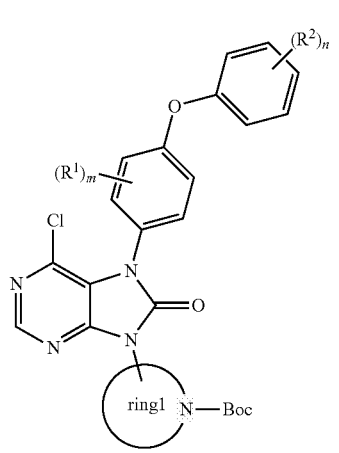

(F)

wherein all symbols represent the same meanings as above;
or a salt thereof;

step (vi): subjecting the compound represented by the formula (F) obtained in the step (v) or a salt thereof to a reaction with a protected amine or a salt thereof to produce a compound represented by the formula (G):

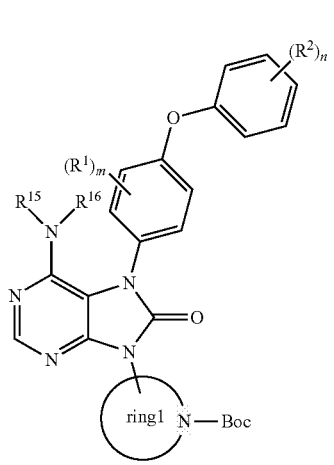

(G)

wherein R15 and R16 respectively and independently represent a hydrogen atom, a benzyloxycarbonyl group, a t-butoxycarbonyl group, an allyloxycarbonyl group, a 1-methyl-1-(4-biphenyl)ethoxycarbonyl group, a trifluoroacetyl group, a 9-fluorenylmethoxycarbonyl group, a benzyl group, a p-methoxybenzyl group, a benzyloxymethyl group or a 2-(trimethylsilyl)ethoxymethyl group, provided that R15 and R16 do not simultaneously represent hydrogen atoms; and all other symbols represent the same meanings as above;
or a salt thereof; and step (vii): subjecting the compound represented by the formula (G) obtained in the step (vi) or a salt thereof to a deprotection reaction to produce the compound represented by the formula (H) or a salt thereof.

2. A method for producing a compound represented by the formula (D):

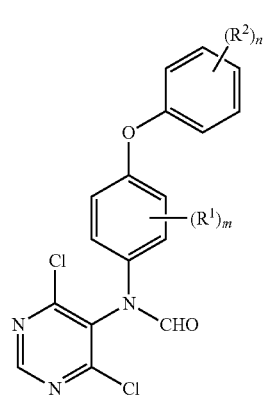

(D)

wherein R1 represents (1) a halogen atom, (2) a C1-4 alkyl group, (3) a C1-4 alkoxy group, (4) a C1-4 haloalkyl group or (5) a C1-4 haloalkoxy group; R2 represents (1) a halogen atom; (2) a C1-4 alkyl group; (3) a C1-4 alkoxy group; (4) a nitrile; (5) a C1-4 haloalkyl group or (6) a C1-4 haloalkoxy group; m represents an integer of 0 to 4; and n represents an integer of 0 to 5;
or a salt thereof,
the method comprising the following steps (i) to (iii):

step (i): subjecting a compound represented by the formula (A):

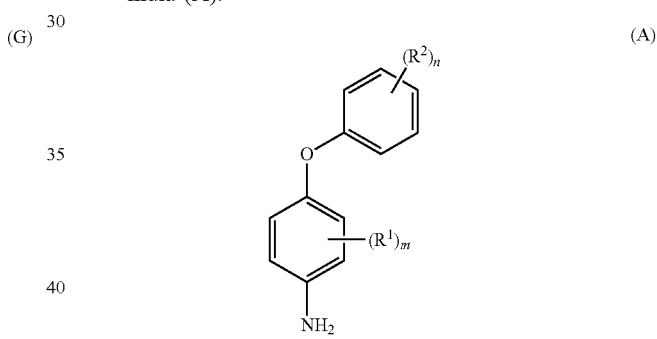

(A)

wherein all symbols represent the same meanings as above;
or a salt thereof to a reaction with a halomalonic diester compound in the presence of a bromide salt, a phase-transfer catalyst and a base to produce a compound represented by the formula (B):

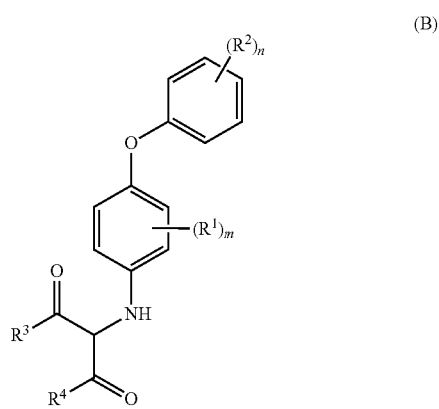

(B)

wherein R3 and R4 respectively and independently represent a C1-3 alkoxy group; and all other symbols represent the same meanings as above;

or a salt thereof;

step (ii): subjecting the compound represented by the formula (B) obtained in the step (i) or a salt thereof to a reaction with a formamidine salt in the presence of a base to produce a compound represented by the formula (C):

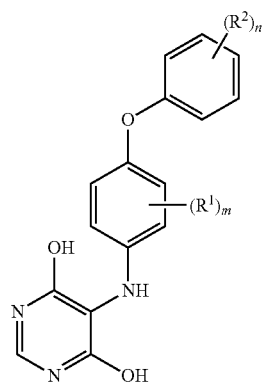

(C)

wherein all symbols represent the same meanings as above;

or a salt thereof; and step (iii): subjecting the compound represented by the formula (C) obtained in the step (ii) or a salt thereof to a reaction with phosphorus oxychloride in the presence of N,N-dimethylformamide to produce the compound represented by the formula (D) or a salt thereof.

3. A method for producing a compound represented by the formula (I):

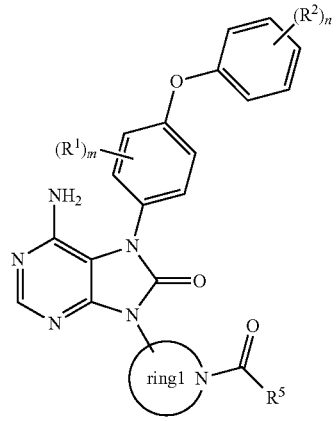

(I)

wherein R1 represents (1) a halogen atom, (2) a C1-4 alkyl group, (3) a C1-4 alkoxy group, (4) a C1-4 haloalkyl group or (5) a C1-4 haloalkoxy group; R2 represents (1) a halogen atom, (2) a C1-4 alkyl group, (3) a C1-4 alkoxy group, (4) a nitrile, (5) a C1-4 haloalkyl group or (6) a C1-4 haloalkoxy group; R5 represents a C2-4 alkenyl group or C2-4 alkynyl group which may be substituted by 1 to 5 substituents selected from the group consisting of (1) NR6R7, (2) a halogen atom, (3) CONR8R9, (4) CO2R10 and (5) OR11; R6 and R7 respectively and independently represent (1) a hydrogen atom or (2) a C1-4 alkyl group which may be substituted by OR12 or CONR13R14; R6 and R7 may form together with a nitrogen atom to which R6 and R7 are attached a 4- to 7-membered nitrogen-containing saturated heterocycle which may be substituted by an oxo group or a hydroxy group; R8 and R9 respectively and independently represent (1) a hydrogen atom, (2) a C1-4 alkyl group or (3) a phenyl group; R10 represents (1) a hydrogen atom or (2) a C1-4 alkyl group; R11 represents (1) a hydrogen atom, (2) a C1-4 alkyl group, (3) a phenyl group or (4) a benzotriazolyl group; R12 represents (1) a hydrogen atom or (2) a C1-4 alkyl group; and R13 and R14 respectively and independently represent (1) a hydrogen atom or (2) a C1-4 alkyl group; ring1 represents an azetidine, pyrrolidine or piperidine ring; m represents an integer of 0 to 4; and n represents an integer of 0 to 5;

or a salt thereof, the method comprising:

step (i): subjecting a compound represented by the formula (A):

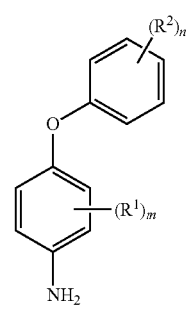

(A)

wherein all symbols represent the same meanings as above;

or a salt thereof to a reaction with a halomalonic diester compound in the presence of a bromide salt, a phase-transfer catalyst and a base to produce a compound represented by the formula (B):

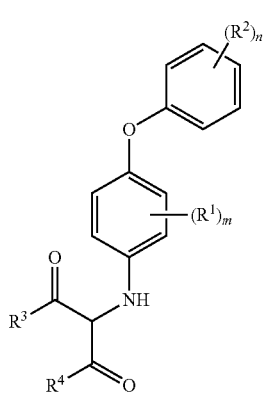

(B)

wherein R3 and R4 respectively and independently represent a C1-3 alkoxy group; and all other symbols represent the same meanings as above;

or a salt thereof;

step (ii): subjecting the compound represented by the formula (B) obtained in the step (i) or a salt thereof to a reaction with a formamidine salt in the presence of a base to produce a compound represented by the formula (C):

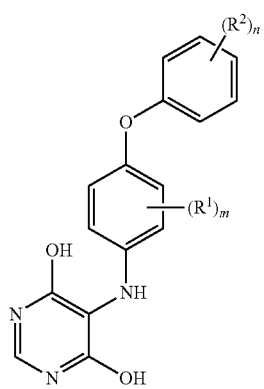

(C)

wherein all symbols represent the same meanings as above;
or a salt thereof;

step (iii): subjecting the compound represented by the formula (C) obtained in the step (ii) or a salt thereof to a reaction with phosphorus oxychloride in the presence of N,N-dimethylformamide to produce a compound represented by the formula (D):

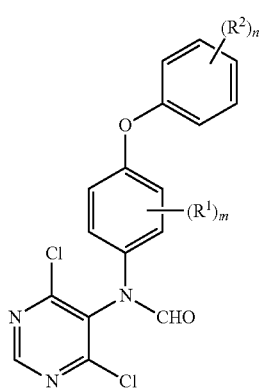

(D)

wherein all symbols represent the same meanings as above;
or a salt thereof;

step (iv): subjecting the compound represented by the formula (D) obtained in the step (iii) or a salt thereof to a reaction with a compound represented by the formula (a):

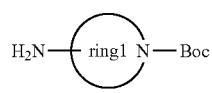

(a)

wherein Boc represents a tert-butoxycarbonyl group and ring1 represents the same meaning as above;

or a salt thereof in the presence of a base followed by alkaline hydrolysis to produce a compound represented by the formula (E):

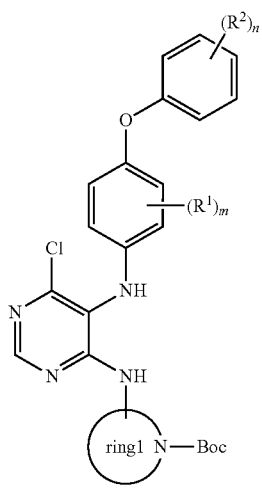

(E)

wherein all symbols represent the same meanings as above;
or a salt thereof;

step (v): subjecting the compound represented by the formula (E) obtained in the step (iv) or a salt thereof to a reaction with 1,1'-carbonyldiimidazole in the presence of a base to produce a compound represented by the formula (F):

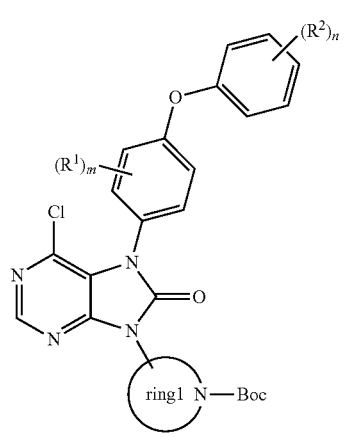

(F)

wherein all symbols represent the same meanings as above;
or a salt thereof;

step (vi): subjecting the compound represented by the formula (F) obtained in the step (v) or a salt thereof to a reaction with a protected amine or a salt thereof to produce a compound represented by the formula (G):

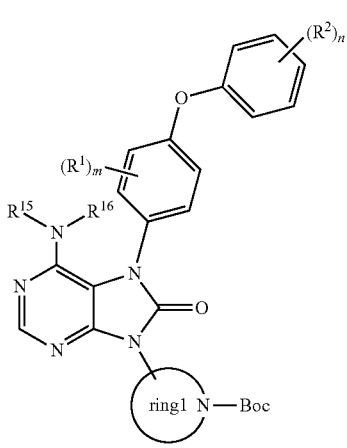

wherein R15 and R16 respectively and independently represent a hydrogen atom, a benzyloxycarbonyl group, a t-butoxycarbonyl group, an allyloxycarbonyl group, a 1-methyl-1-(4-biphenyl)ethoxycarbonyl group, a trifluoroacetyl group, a 9-fluorenylmethoxycarbonyl group, a benzyl group, a p-methoxybenzyl group, a benzyloxymethyl group or a 2-(trimethylsilyl) ethoxymethyl group, provided that R15 and R16 do not simultaneously represent hydrogen atoms; and all other symbols represent the same meanings as above;

or a salt thereof;

step (vii): subjecting the compound represented by the formula (G) obtained in the step (vi) or a salt thereof to a deprotection reaction to produce the compound represented by a formula (H):

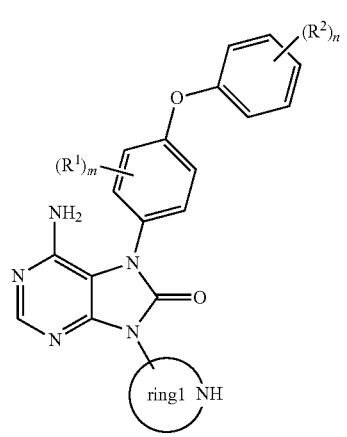

wherein all symbols represent the same meanings as above;

or a salt thereof; and step (viii): subjecting the compound represented by the formula (H) obtained in the step (vii) or a salt thereof to an amidation reaction with a compound represented by the formula (b):

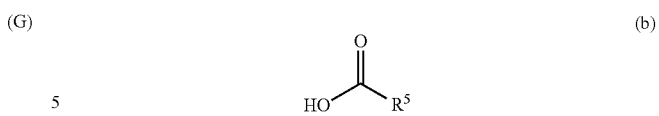

wherein all symbols represent the same meanings as above;

or a salt thereof in the presence of 2,4,6-tripropyl-1,3,5, 2,4,6-trioxatriphosphorinan-2,4,6-trioxide to produce the compound represented by the formula (I) or a salt thereof.

4. N-(4,6-dichloropyrimidin-5-yl)-N-(4-phenoxyphenyl) formamide.

5. Tert-butyl (3R)-3-[6-(benzylamino)-8-oxo-7-(4-phenoxyphenyl)-7,8-dihydro-9H-purin-9-yl]pyrrolidine-1-carboxylate.

6. The method for producing a compound according to claim 3, wherein the compound represented by the formula (I) is 6-amino-9-[(3R)-1-(2-butynoyl)-3-pyrrolidinyl]-7-(4-phenoxyphenyl)-7, 9-dihydro-8H-purin-8-one.

7. A method for producing 6-amino-9-[(3R)-1-(2-butynoyl)-3-pyrrolidinyl]-7-(4-phenoxyphenyl)-7,9-dihydro-8H-purin-8-one or a salt thereof, the method comprising:

step (i): subjecting 4-phenoxyaniline or a salt thereof to a reaction with diethyl chloromalonate in the presence of a bromide salt, a phase-transfer catalyst and a base to produce diethyl [(4-phenoxyphenyl)amino]propanediate or a salt thereof;

step (ii): subjecting diethyl [(4-phenoxyphenyl)amino] propanediate obtained in the step (i) or a salt thereof to a reaction with a formamidine salt in the presence of a base to produce 5-[(4-phenoxyphenyl)amino]pyrimidine-4,6-diol or a salt thereof;

step (iii): subjecting 5-[(4-phenoxyphenyl)amino]pyrimidine-4,6-diol obtained in the step (ii) or a salt thereof to a reaction with phosphorus oxychloride in the presence of N,N-dimethylformamide to produce N-(4,6-dichloropyrimidin-5-yl)-N-(4-phenoxyphenyl)formamide or a salt thereof;

step (iv): subjecting N-(4,6-dichloropyrimidin-5-yl)-N-(4-phenoxyphenyl)formamide obtained in the step (iii) or a salt thereof to a reaction with tert-butyl (3R)-3-aminopyrrolidine-1-carboxylate or a salt thereof in the presence of a base followed by alkaline hydrolysis to produce tert-butyl (3R)-3-({6-chloro-5-[(4-phenoxyphenyl)amino]pyrimidin-4-yl}amino)pyrrolidine-1-carboxylate or a salt thereof;

step (v): subjecting tert-butyl (3R)-3-({6-chloro-5-[(4-phenoxyphenyl)amino]pyrimidin-4-yl}amino)pyrrolidine-1-carboxylate obtained in the step (iv) or a salt thereof to a reaction with 1,1'-carbonyldiimidazole in the presence of a base to produce tert-butyl (3R)-3-[6-chloro-8-oxo-7-(4-phenoxyphenyl)-7,8-dihydro-9H-purin-9-yl]pyrrolidine-1-carboxylate or a salt thereof;

step (vi): subjecting tert-butyl (3R)-3-[6-chloro-8-oxo-7-(4-phenoxyphenyl)-7,8-dihydro-9H-purin-9-yl]pyrrolidine-1-carboxylate obtained in the step (v) or a salt thereof to a reaction with benzylamine or a salt thereof to produce tert-butyl (3R)-3-[6-(benzylamino)-8-oxo-7-(4-phenoxyphenyl)-7,8-dihydro-9H-purin-9-yl]pyrrolidine-1-carboxylate or a salt thereof;

step (vii): subjecting tert-butyl (3R)-3-[6-(benzylamino)-8-oxo-7-(4-phenoxyphenyl)-7,8-dihydro-9H-purin-9-yl]pyrrolidine-1-carboxylate obtained in the step (vi) or a salt thereof to a deprotection reaction to produce 6-amino-7-(4-phenoxyphenyl)-9-[(3R)-pyrrolidin-3-yl]-7,9-dihydro-8H-purin-8-one or a salt thereof; and step (viii): subjecting 6-amino-7-(4-phenoxyphenyl)-9-[(3R)-pyrrolidin-3-yl]-7,9-dihydro-8H-purin-8-one obtained in the step (vii) or a salt thereof to an amidation reaction with 2-butynoic acid or a salt thereof in the presence of 2,4,6-tripropyl-1,3,5,2,4,6-trioxatriphosphorinan-2,4,6-trioxide to produce 6-amino-9-[(3R)-1-(2-butynoyl)-3-pyrrolidinyl]-7-(4-phenoxyphenyl)-7,9-dihydro-8H-purin-8-one or a salt thereof.

* * * * *